US009089711B2

(12) United States Patent
Giorgis et al.

(10) Patent No.: US 9,089,711 B2
(45) Date of Patent: *Jul. 28, 2015

(54) VENTRICULAR CAPTURE TESTING BY ANALYSIS OF AN ENDOCARDIAL ACCELERATION SIGNAL IN AN ACTIVE IMPLANTABLE MEDICAL DEVICE

(71) Applicant: SORIN CRM S.A.S., Clamart (FR)

(72) Inventors: Lionel Giorgis, Saint Brieuc (FR); Amel Amblard, Chatenay-Malabry (FR)

(73) Assignee: SORIN CRM S.A.S., Clamart (FR)

( * ) Notice: Subject to any disclaimer, the term of this patent is extended or adjusted under 35 U.S.C. 154(b) by 31 days.

This patent is subject to a terminal disclaimer.

(21) Appl. No.: 13/942,596

(22) Filed: Jul. 15, 2013

(65) Prior Publication Data

US 2013/0304144 A1    Nov. 14, 2013

Related U.S. Application Data

(63) Continuation of application No. 13/190,951, filed on Jul. 26, 2011, now Pat. No. 8,489,188.

(30) Foreign Application Priority Data

Jul. 26, 2010  (FR) ...................................... 10 56098

(51) Int. Cl.
*A61N 1/00*        (2006.01)
*A61N 1/37*        (2006.01)
(Continued)

(52) U.S. Cl.
CPC .............. *A61N 1/3702* (2013.01); *A61N 1/371* (2013.01); *A61N 1/3925* (2013.01); *G06K 9/00536* (2013.01); *A61N 1/36578* (2013.01)

(58) Field of Classification Search
CPC .. A61N 1/36578; A61N 1/371; A61N 1/3925

USPC ................................ 600/508–521; 607/4–28
See application file for complete search history.

(56) References Cited

U.S. PATENT DOCUMENTS 5,411,533 A    5/1995  Dubreuil et al.
6,181,968 B1   1/2001  Limousin
(Continued)

FOREIGN PATENT DOCUMENTS

EP    0 515 319 A2   11/1992
EP    0 935 979 A1    8/1999
(Continued)

OTHER PUBLICATIONS

European Search Report mailed Jul. 14, 2011, as received in corresponding European Patent Application No. 11164811.7.
(Continued)

*Primary Examiner* — Scott Getzow
(74) *Attorney, Agent, or Firm* — Foley & Lardner LLP

(57) ABSTRACT

A processor-based method for use with an active implantable medical device for cardiac pacing, resynchronization, and/or defibrillation includes forming a plurality of first and second endocardial acceleration vectors using a plurality of endocardial acceleration signals acquired using stimulation to cause capture and a spontaneous rhythm of the patient in the absence of ventricular pacing, respectively. An at least two dimension space is created using the first and second endocardial acceleration vectors, including two subspaces corresponding to the presence and absence of capture, respectively. Ventricular capture is tested for after acquiring a new endocardial acceleration signal. The testing includes forming a new endocardial acceleration signal based on the new vector. Presence or absence of capture is determined for the new signal based on the position of the new vector relative to the two subspaces.

20 Claims, 4 Drawing Sheets

(51) Int. Cl.
*G06K 9/00* (2006.01)
*A61N 1/39* (2006.01)
*A61N 1/365* (2006.01)

(56) References Cited

U.S. PATENT DOCUMENTS

| | | |
|---|---|---|
| 6,487,451 B1 | 11/2002 | Casset et al. |
| 2004/0260351 A1 | 12/2004 | Holmstrom et al. |
| 2008/0021336 A1 | 1/2008 | Dobak, III |
| 2009/0209875 A1 | 8/2009 | Giorgis et al. |
| 2009/0281590 A1 | 11/2009 | Maskara et al. |
| 2010/0023082 A1 | 1/2010 | Dong et al. |
| 2010/0125308 A1 | 5/2010 | Casset |

FOREIGN PATENT DOCUMENTS

| | | |
|---|---|---|
| EP | 1 080 744 A1 | 3/2001 |
| EP | 1 995 685 A2 | 11/2008 |
| EP | 2 092 885 A1 | 8/2009 |
| EP | 2 189 180 A1 | 5/2010 |
| WO | WO-93/02741 A1 | 2/1993 |
| WO | WO-2005/089866 A1 | 9/2005 |

OTHER PUBLICATIONS

Haykin, Simon, *Neural Networks: A Comprehensive Foundation (Second Edition)*, Jul. 16, 1998, pp. 1-823, Prentice Hall, India.

Bishop, Christopher M., Neural Networks for Pattern Recognition, Oxford University Press, 1995.

Preliminary Search Report for French Patent Application No. 1056098, dated Feb. 2, 2010, 2 pages.

(STIMULATED RHYTHM)

(SPONTANEOUS RHYTHM)

VENTRICULAR CAPTURE TESTING BY ANALYSIS OF AN ENDOCARDIAL ACCELERATION SIGNAL IN AN ACTIVE IMPLANTABLE MEDICAL DEVICE

CROSS REFERENCE TO RELATED APPLICATIONS

The present application is a continuation of U.S. application Ser. No. 13/190,951 entitled "Ventricular Capture Testing By Analysis Of An Endocardial Acceleration Signal In An Active Implantable Medical Device", filed on Jul. 26, 2011, which claims the benefit of and priority to French application Ser. No. 10/56098 entitled "Active Implantable Medical Device Such As A Cardiac Prosthesis, Including Means Of Ventricular Capture Testing By Analysis Of An Endocardial Acceleration Signal" and filed Jul. 26, 2010. Both U.S. Ser. No. 13/190,951 and FR 10/56098 are hereby incorporated by reference in their entireties.

FIELD

The present invention relates to "active implantable medical devices" as defined by the 20 Jun. 1990 Directive 90/385/EEC of the Council of the European Communities, and more specifically to devices that continuously monitor a patient's cardiac rhythm and deliver to the heart electrical stimulation pulses for pacing. Cardiac resynchronization, cardioversion and/or defibrillation is provided, as necessary, in response to a rhythm disorder detected by the device.

BACKGROUND

Active implantable medical devices typically include circuits that provide ventricular pacing by delivering stimulation pulses of low energy to different electrodes implanted in the right and/or left ventricle. After the delivery of the stimulation pulse, it is important for the device to collect (detect) the wave of depolarization induced by the stimulation of the ventricle, also called an "evoked wave," and test for whether the delivered stimulation pulse was effective. This detection, also called the "capture test," is used in particular to assess the minimum level of stimulation pulse energy needed to cause depolarization of the ventricle, the so-called "pacing threshold." It is typically necessary to adjust the amplitude and/or width of the stimulation pulse in order to ensure that, first, a stimulation pulse causes an effective evoked wave, i.e., a "capture," and, second, the delivered energy is not too excessive, so as not to reduce unnecessarily the life of the device due to excessive consumption of energy.

The capture test is also important for monitoring the operation of those devices that deliver cardiac resynchronization therapy (called "CRT"), which are devices equipped with electrodes to stimulate both ventricles. A CRT device can monitor the patient's cardiac rhythm and deliver if necessary pulses to stimulate jointly the left and right ventricles so as to resynchronize them. These respective stimuli are applied with a variable interventricular delay (WD), which can be positive or negative, and adjusted to resynchronize the contractions of the ventricles and optimize the patient's hemodynamic status. The capture test procedure must ensure that stimulation is effective on the left and the right ventricles because it is an essential condition for their resynchronization. Yet, there are generally different pacing thresholds for the left and right ventricular stimulation sites, which if not accounted for can lead to a defective stimulation. In addition, the device may be confused by detection of an electrostimulated depolarization in the analyzed site, or by a depolarization wave conducted from the nearby site that is indirectly captured, which if not accounted for may result in an erroneous detection of the depolarization waves.

Finally, any change in the interventricular delay may result in a change in the capture test parameters, so it is essential to very accurately follow the operation of the device at each adjustment of the interventricular delay to ensure that the resynchronization therapy is efficient.

There are many techniques known for performing a ventricular capture test. Such techniques are described, for example, in WO 93/02741 A1 and its counterpart U.S. Pat. No. 5,411,533, and in EP 0935979 A1 and its counterpart U.S. Pat. No. 6,181,968 (both assigned to Sorin CRM S.A.S, previously known as ELA Medical), and are based on an analysis of the electrical signals collected by the device.

More recently it has been proposed to test for capture from a signal delivered by a sensor directly detecting the mechanical contraction of the myocardium, which provides immediate information on the response to ventricular pacing, ignoring blanking periods and other limitations inherent in the collection of an electrical signal. In other words, it consists in using a functional signal representative of the cardiac mechanics, instead of a signal due to the electrical propagation of the evoked depolarization wave.

WO2005/089866 A1 (assigned to Medtronic, Inc.) proposes to use a mechanical contraction sensor in a CRT device for various purposes such as: optimization of the atrioventricular delay (AVD) used for dual chamber pacing, optimization of the interventricular delay (VVD) used for biventricular stimulation for a resynchronization therapy CRT and, alternatively, the discrimination between capture and loss of capture (i.e., when no evoked wave is detected in response to a delivered stimulation pulse) in one or more chambers of the heart during delivery of the stimulation therapy.

U.S. Patent Publication No. 2004/0260351 A1 (Holmstrom et al.) proposes, meanwhile, a detector of an evoked response for a biventricular pacing device, in which a signal of cardiac bioimpedance (or, alternatively, an acceleration signal) is subjected to a morphological analysis to discriminate between effective capture and loss of capture.

For this, the device measures (by a method of least squares applied to successively collected samples over a predetermined time window) the Euclidean distances between, on one hand, the impedance signal collected after each double stimulation and, on the other hand, five reference templates, each corresponding to one of the five following predetermined situations: (i) capture in both ventricles; (ii) capture on the left ventricle only, (iii) capture on the right ventricle only, (iv) loss of capture in both ventricles; and (v) intrinsic conduction in the absence of stimulation. The five distances thus determined are compared with respective distance thresholds for classification decisions between capture/loss of capture.

This technique has the disadvantage that the decision regarding the existence and configuration of the captures is taken in reference to a distance, a value that must be relativized and adapted, (from what value do we consider that the signal complies with one of the templates?), the thresholds to which the Euclidean distances are compared being very patient-dependent parameters. Another drawback of this technique is that, as often happens in the biomedical field, the signals compared in pairs (collected signal vs. templates) are not synchronous signals. Thus, if one calculates a distance between two signals shifted by even a small value (e.g., 5 ms), a very large bias may be introduced into the calculation of distance, said bias being present even when the two signals are identical, and thus distort the measurement and the capture test result.

EP 1995685 A2 (Biotronik) describes a method wherein the capture is detected based on predetermined templates and a similarity calculation by distance calculations.

U.S. Patent Publication No. 2008/021336 A1 (assigned to Cardiosync) describes a technique of capture detection based on the extraction of endocardiac acceleration signals for summarizing the characteristic pattern (signature) of the signal, and a detection of the possible capture by means of a unique parameter derived from the pattern.

OBJECT AND SUMMARY

It is therefore an object of the present invention to propose an improved capture detection technique that is based on a normalized indicator, is not patient-dependent and is insensitive to even large time shifts that may affect the signals to be compared and allows one to estimate the value of this time shift.

It is a further object of the present invention to propose a capture detection technique that is equally applicable to the detection of a capture on a single ventricle (right as well as left) as well as a biventricular capture detection (for a CRT device) and that can be implemented with relatively modest software resources, preferably within an already implanted device in real time.

The present invention is based on an analysis of the endocardial acceleration (hereinafter "EA"), which is a parameter that reflects very accurately and in real time the mechanical phenomena involved in the functioning of the patient's myocardium. EA can be measured by an accelerometer directly in contact with the heart muscle, as described, e.g., in EP 0515319 A1 (assigned to Sorin Biomedica Cardio SpA), the disclosure of which is incorporated herein by reference. EP0515319A1 teaches to collect an EA signal using a endocardial lead provided with a distal stimulation electrode implanted at the apex of the ventricle and including a microaccelerometer to measure the endocardial acceleration.

It should be noted, however, that although the present description mainly refers to the analysis of an EA signal delivered by a sensor placed on an endocardial lead, the invention is equally applicable to an analysis conducted from an EA signal delivered by other types of implanted sensors, such as a myocardial wall motion sensor or an epicardial sensor. The invention also is applicable to the analysis of an EA signal obtained external to the implanted device, for example, noninvasively collected from a sensor attached to the patient's chest at the sternum.

The EA signal collected during a cardiac cycle forms at least two major components, corresponding to the two major heart sounds, the so-called "S1" and "S2" sounds of the phonocardiogram. It is thus possible to recognize in each cardiac cycle:

(i) The first component of endocardial acceleration ("EA1"), whose amplitude variations are closely linked to the changes in pressure in the ventricle (the maximum peak-to-peak amplitude of this component EA1, called PEA1, being specifically correlated to the positive maximum pressure variation dP/dt in the left ventricle) and may therefore be a parameter representative of the myocardial contractility, itself linked to the level of activity of the sympathetic system; and (ii) The second component of endocardial acceleration ("EA2") which occurs during the phase of isovolumetric ventricular relaxation. This second component is mainly produced by the closure of the aortic and pulmonary valves.

More specifically, the present invention proposes an implantable medical device comprising in a manner in itself known, e.g., from U.S. Patent Publication No. 2008/021336 A1 referenced above: ventricular pacing means for delivering low energy stimulation pulses to be applied to an electrode implanted in the right and/or left ventricular cavities, and means for testing the ventricular capture, able to detect the: onset of ventricular contraction resulting from the application of a stimulation pulse. The means for testing ventricular capture include: an acceleration sensor having as an output a signal representative of the EA movements produced by the cyclical contractions of the ventricle, and means for analyzing the signal delivered by the EA sensor (the "EA signal") for determining in response the presence/absence of ventricular capture.

In a preferred embodiment, the means for analyzing the EA signal comprises means for isolating in the EA signal at least one EA component of endocardial acceleration corresponding to the first and/or second major noises of the heart, this EA component describing a continuous variation of the EA signal in a limited temporal window corresponding to a fraction of a cardiac cycle; means for extracting from the isolated EA component n indicators, with n=2, representative of the EA signal; and means for forming an n dimension EA vector from the indicators thus extracted.

The device also preferably includes classifier means for, during a preliminary phase: acquiring a plurality of EA signals at a stimulation energy level high enough to cause a capture and form a corresponding plurality of first reference EA vectors; acquiring a plurality of EA signals in spontaneous rhythm of the patient in the absence of ventricular pacing and forming a corresponding plurality of second reference EA vectors; and from the first and second acquired EA vectors, partitioning the n-dimension space of the EA vectors into two subspaces respectively corresponding to the presence and absence of a capture (i.e., a capture and a loss of capture).

The means for testing ventricular capture also includes means for acquiring at least one EA signal at a current level of stimulation energy, and forming at least one corresponding current EA vector; and means for discriminating the presence or absence of capture based on the current position of the EA vector in the n-dimension space of EA vectors, respectively in one or the other of these two subspaces.

The n indicators representative of the EA signal can be chosen in particular from among the group consisting of the value of the peak-to-peak amplitude, the width, the moment of occurrence of the peak, the start time, and the moment of completion, of the EA component, where the EA component may be the EA1 component, the EA2 component, the EA3 component and/or the EA4 component, or any combination of the indicators for any of the foregoing components.

Alternatively, it is also possible to select morphology indicators from among the group consisting of the Signal to Noise Ratio (SNR), the contrast value, the entropy value, and the combined energy of the EA component, where again the EA component may be the EA1 component, the EA2 component, the EA3 component and/or the EA4 component, or any combination of the indicators for any of the foregoing components.

In a preferred embodiment, n=2 and the two representative indicators of the EA signal are the value of the peak-to-peak amplitude and the width of the EA1 component.

Preferably, a threshold criterion may be applied separately to each of the indicators of the EA vectors, and the presence or absence of a capture may be discriminated by combining the output of the thresholding step, for example a vote (e.g., if both indicators cross their associated threshold, then capture is confirmed).

In preferred embodiment, the means for partitioning the n-dimension space of EA vectors into two sub-areas include means for implementing a classification algorithm selected from among the group consisting of: K-nearest neighbors, neural network, and linear classification by estimation of the pseudo-inverse matrix. In one embodiment, the classifier means further comprise means for evaluating a distance between classes and verification of a minimum distance.

The device of the present invention preferably also comprises means for performing atrial stimulation, activated at a predetermined fixed stimulation frequency during the implementation of the classifier means and the means for testing ventricular capture.

In one embodiment, the device comprises means for searching the threshold of ventricular capture, for iteratively modifying the energy level of the stimulation pulse, and testing each iteration for the presence or absence of a capture.

In another embodiment, the device comprises means for jointly stimulating the left and right ventricles, with an application of an interventricular delay between the respective times of stimulation of the right and left ventricles, wherein the means for testing ventricular capture comprises means for detecting the presence of a capture on each of the right and left ventricles; and the device includes means for activating the means for testing ventricular capture in response to any adjustment, e.g., a variation or modification, of the interventricular delay.

Preferably, the acceleration sensor is a sensor selected from among the group consisting of an intracardiac sensor; an epicardial sensor; and an external sensor.

One embodiment of the present disclosure relates to a processor-based method for use with an active implantable medical device for cardiac pacing, resynchronization and/or defibrillation. The method includes forming a plurality of first reference endocardial acceleration vectors using a plurality of endocardial acceleration signals acquired using stimulation to cause capture. The method further includes forming a plurality of second reference endocardial acceleration vectors using a plurality of endocardial acceleration signals acquired in a spontaneous rhythm of the patient in the absence of ventricular pacing. The method further includes creating at least a two dimensional space using the first reference endocardial acceleration vectors and the second reference endocardial acceleration vectors, wherein the at least two dimensional space includes two subspaces corresponding to the presence and absence of capture, respectively. The method further includes testing for ventricular capture after acquiring a new endocardial acceleration signal, wherein the testing includes forming a new endocardial acceleration vector for the new endocardial acceleration signal, and wherein the testing further includes determining the presence or absence of capture for the new endocardial acceleration signal based on the position of the new endocardial acceleration vector relative to the two subspaces of the at least two dimensional space.

Another embodiment of the present disclosure relates to a system for testing ventricular capture following delivery of a stimulation pulse from an active implantable medical device for cardiac pacing, resynchronization and/or defibrillation. The system includes the implantable medical device capable of delivering a stimulation pulse and an acceleration sensor for generating an endocardial acceleration signal representative of a patient's endocardiac acceleration. The system further includes a processor. The processor is configured to form a plurality of first reference endocardial acceleration vectors using a plurality of endocardial acceleration signals acquired by the acceleration sensor when using stimulation sufficient to cause capture. The processor is further configured to form a plurality of second reference endocardial acceleration vectors using a plurality of endocardial acceleration signals acquired by the acceleration sensor in a spontaneous rhythm of the patient in the absence of ventricular pacing. The processor is further configured to create at least a two dimensional space using the first reference endocardial acceleration vectors and the second reference endocardial acceleration vectors, wherein the at least two dimensional space includes two subspaces corresponding to the presence and absence of capture, respectively. The processor is further configured to test for ventricular capture after acquiring a new endocardial acceleration signal, wherein the testing includes forming a new endocardial acceleration vector for the new endocardial acceleration signal, and wherein the testing further includes determining the presence or absence of capture for the new endocardial acceleration signal based on the position of the new endocardial acceleration vector relative to the two subspaces of the at least two dimensional space.

Yet another embodiment of the present disclosure relates to a method of creating a multi-dimensional space comprising two subspaces corresponding to the presence and absence of capture for use in determining the effectiveness of a delivered stimulation pulse. The method includes delivering stimulation having sufficient energy to cause capture. The method further includes acquiring a first plurality of endocardial acceleration signals for a plurality of cardiac cycles following the delivery of stimulation. The method further includes extracting at least two indicators from the first plurality of endocardial acceleration signals. The method further includes acquiring a second plurality of endocardial acceleration signals for a plurality of cardiac cycles during a spontaneous rhythm of the patient in the absence of stimulation. The method further includes extracting at least two indicators from the second plurality of endocardial acceleration signals. The method further includes creating a plurality of first reference endocardial acceleration vectors in a multi-dimensional space based on the at least two indicators from the first plurality of endocardial acceleration signals. The method further includes creating a plurality of second reference endocardial acceleration vectors in a multi-dimensional space based on the at least two indicators from the second plurality of endocardial acceleration signals. The method further includes defining two subspaces corresponding to the presence and absence of capture based on a rule for separating the plurality of first reference endocardial acceleration vectors from the plurality of second reference endocardial acceleration vectors.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which.

DETAILED DESCRIPTION

An example of realization of the device according to the invention will now be described with reference to the drawings FIGS. 1-7.

As regards to its software aspects, the present invention can be implemented by an appropriate programming of the control software of a known device, for example, a cardiac pacemaker or a defibrillator/cardioverter, including methods for collecting a signal provided by endocardial leads and/or one or more implanted sensors. The present invention may particularly be applied to implantable devices such as those of the Reply and Paradym device families produced and marketed by Sorin CRM, Clamart France, formerly known as ELA Medical, Montrouge, France.

These devices include programmable microprocessor circuitry to receive, format, and process electrical signals collected (detected) by implanted electrodes and deliver stimulation pulses to these electrodes. It is possible to transmit by telemetry software that will be stored in a memory of the implantable devices and executed to implement the functions of the present invention' that will be described herein. The adaptation of these devices to implement the functions and features of the present invention is believed to be within the abilities of a person of ordinary skill in the art, and therefore will not be described in detail.

Principle of Analysis of an EA Component

As the mentioned above, the endocardial acceleration EA signal collected during a cardiac cycle includes two major components, corresponding to the two major heart sounds (S1 and S2 sounds of the phonocardiogram) that can be recognized in each cardiac cycle:

The first component of endocardial acceleration ("EA1"), whose amplitude variations are closely linked to changes in pressure in the ventricle (the maximum peak-to-peak amplitude of this component EA1, called PEA1, being specifically correlated to the positive maximum pressure variation dP/dt in the left ventricle) and may therefore be a parameter representative of the myocardial contractility, itself linked to the level of activity of the sympathetic system;

The second component of endocardial acceleration ("EA2") which, in turn, occurs during the phase of isovolumetric ventricular relaxation. This second component is mainly produced by the closure of the aortic and pulmonary valves.

The EA signal may contain one or two other components, called EA3 and EA4, corresponding to the known sounds S3 and S4 of the phonocardiogram.

Figure 1:
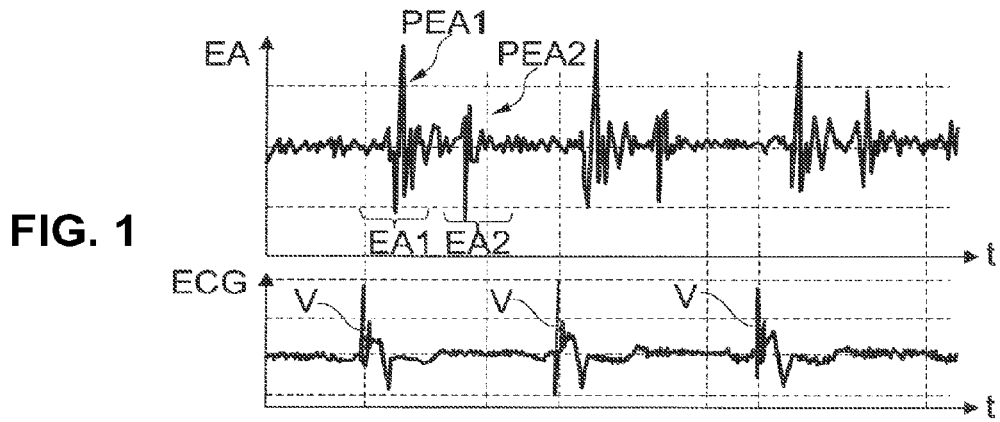
FIG. 1 illustrates representative timing diagrams recorded during three successive cardiac cycles of an endocardial acceleration EA signal and a corresponding electrocardiogram ECG tracing.

The EA signal shown in FIG. 1 shows the timings identified in three successive cardiac cycles of an EA endocardial acceleration signal and a corresponding electrocardiogram ECG plot. The preliminary processing of the EA component involves, first, to distinguish the successive cardiac cycles in the continuously collected EA signal, by identifying markers at the beginning of the cycle to separate the cycles and to isolate a series of EA sub-signals bounded in time, each corresponding to a duration of one cardiac cycle. In the case of an endocardial EA signal, the time markers at the beginning of the cycle are provided by the implant itself, which memorizes the moments of stimulation V, as shown in FIG. 1, or the moment of detection R of the R-wave (depending on the mode of operation at the time). Further, in the case of an external EA signal, the time markers at the beginning of the cardiac cycle are provided by an algorithm to detect peaks of stimulation or QRS complexes of the ECG signal, which signal is collected by external electrodes.

The next step is to isolate the EA1 and/or EA2 component in each subsignal bounded in time corresponding to a cardiac cycle.

In the description which follows, the present invention is described mainly with respect to the EA1 component because this is the most distinct characteristic. However, it should be understood that the teachings of the invention are equally transferable to an analysis of the EA2 component, alternatively or in addition to the EA1 component. In this regard, each of the EA1 and EA2 "components" are represented by a set of values describing the continuous variation of the EA signal in a given time window extending around the PEA1 and PEA2 peaks, respectively, for a fraction of the duration of a cardiac cycle. Specifically, each component consists of a subset of the matrix of N signal samples obtained after scanning the EA signal for the duration of the cardiac cycle. Each component thus represents a fraction of the EA signal for the duration of a cardiac cycle.

Specifically, each component consists of a subset of the matrix of N samples of the EA signal obtained after scanning it over the duration of the cardiac cycle. Each component thus represents a fraction of the EA signal for the duration of a cardiac cycle, and each cardiac cycle is constituted by a plurality of "components" that follow, especially the first two EA1 and EA2 components, these components also being followed by the secondary EA3 and EA4 components.

Preferably, the EA1 (and/or EA2) component of the EA signal is determined after averaging over several cycles, typically from three to five cycles, using a technique such as that described in EP 2092885 A1 and its counterpart US Patent Publication No. 2009/0209875 (both assigned to Sorin CRM S.A.S, previously known as ELA Medical), the disclosures of which are incorporated herein by reference, to eliminate cycle to cycle variations by temporally readjusting the successive components before averaging them. Essentially, this technique performs a preprocessing of the continuously collected EA signal, with:

Division of the EA signal into sub-signals, each corresponding to the duration of a cardiac cycle and identified by a marker at the beginning of a cycle to achieve this division;

Segmentation of each of these sub-signals to individualize one or more of the EA1 and/or EA2 components in a given temporal window;

For the current EA1 or EA2 component thus isolated on a cycle, finding of a autocorrelation peak compared to the EA1 (or EA2) components of the other collected cycles;

Calculation of a corresponding time shifting, and

Application of the calculated time shifting to the current component, so as to align it with the others.

Averaging and analysis processing can then be performed on these successive EA1 (and/or EA2) components, eliminating the bias of the cycle to cycle variability as a result of the pre-processing.

Definition of the Discrimination Classes Between Capture and Non-Capture

This phase of the present invention is to predetermine a distinguishing criterion for recognizing the presence or absence of a capture by defining two corresponding classes that are then used for the capture test itself: depending on whether the current values recorded during a cardiac cycle belong to either of these two classes, it is assumed that there is presence or absence of a capture.

These classes are defined by a partition of an n-dimensional space into two subspaces, one corresponding to a situation of capture, the other to a situation of non-capture. Each of the n dimensions corresponds to a characteristic indicator of the EA component. For clarity and simplicity of presentation, "EA component" is referred to as the component "EA1", but what is said about this "EA1" component should be considered applicable mutatis mutandis to the component EA2, and indeed even possibly to EA3 and/or EA4 components.

The term "indicator" should be understood to be a measurable quantity of the EA1 component, obtained by analyzing the EA signal in a time window corresponding to a limited portion of a cardiac cycle including this EA1 component. The indicator is expressed as a single measured value, that is to say a scalar. Each indicator is chosen to characterize by the value it takes in the absence or presence of a capture.

Specifically, the analysis of one of these indicators (e.g., the PEA1 value of peak to peak amplitude of the EA1 component) is not sufficient to reliably discriminate between presence and absence of a capture, and if used alone would lead to an excessive number of erroneous determinations, with both false positive and false negative results. Therefore, the present invention proposes to use at least two and more preferably a plurality of different indicators characterizing a same EA1 component collected during a given heartbeat, and to combine these indicators between them, according to the method presented below, to decide between the presence or the absence of a capture with a higher degree of reliability.

The set of values all of these various indicators obtained for a given EA1 component of a heart beat (this component being possibly averaged over several successive cycles, as outlined above) is hereafter called "vector."

In the example that follows, the simplest example is taken, a vector of dimension n=2, with the two following indicators, which can simply describe the morphology of the EA1 component in a very different way depending on whether or not there is a capture:

the PEA1 value of the peak-to-peak amplitude of the EA1 component on the analysis window in question, for example, on the window [0-300 ms], the origin of time (0 ms) corresponding to the moment of the last ventricular pacing, and The LEA1 value of the "width" of the EA1 component, that is to say the duration thereof.

Figure 2A:
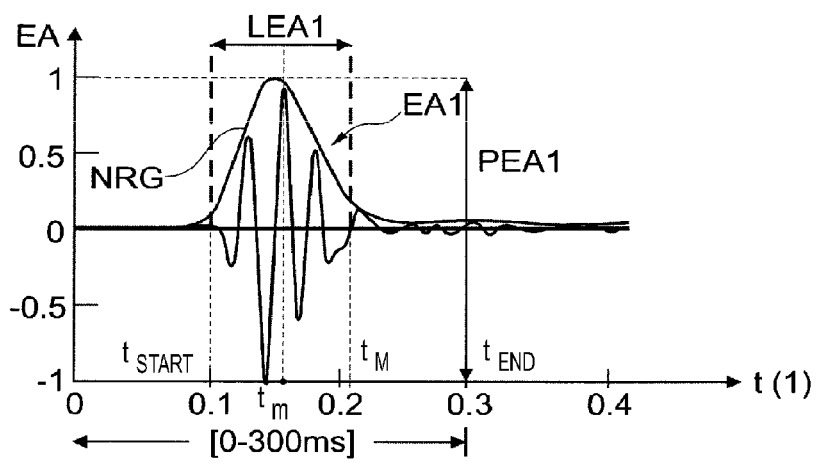
FIGS. 2a and 2b illustrate representative EA components, respectively in the presence of a stimulated rhythm with capture and in the case of a spontaneous rhythm.
Figure 2B:
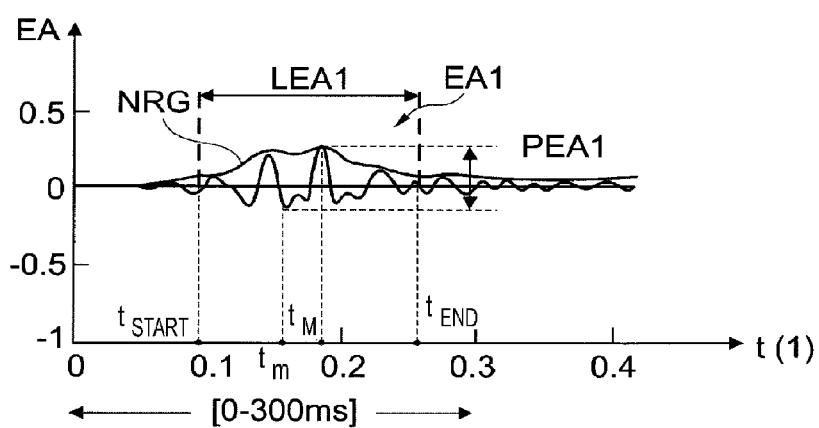

These indicators are illustrated in particular in FIGS. 2a and 2b, respectively, for an EA1 component obtained in stimulated rhythm with capture, and for an EA1 component obtained in spontaneous rhythm.

Specifically with regard to the LEA1 indicator, it can be obtained by thresholding an NRG envelope of energy obtained by squaring the value of signal samples and then applying a smoothing window of, for example, 100 ms. See e.g., FIGS. 2a and 2b. The start time $t_{start}$ and the end time $t_{end}$ of the EA component (with LEA1=$t_{end}$-$t_{start}$) correspond to the crossing of a threshold which can be, for example, 10% of the NRG maximum energy on the window [0-300 ms]. This method of determination of the characteristic instants of the EA1 component is described, as well as others, in EP 2092885 A1 and its counterpart US Patent Publication No. 2009/0209875 cited above, incorporated by reference herein, which can be referred to for more details.

Figure 4:
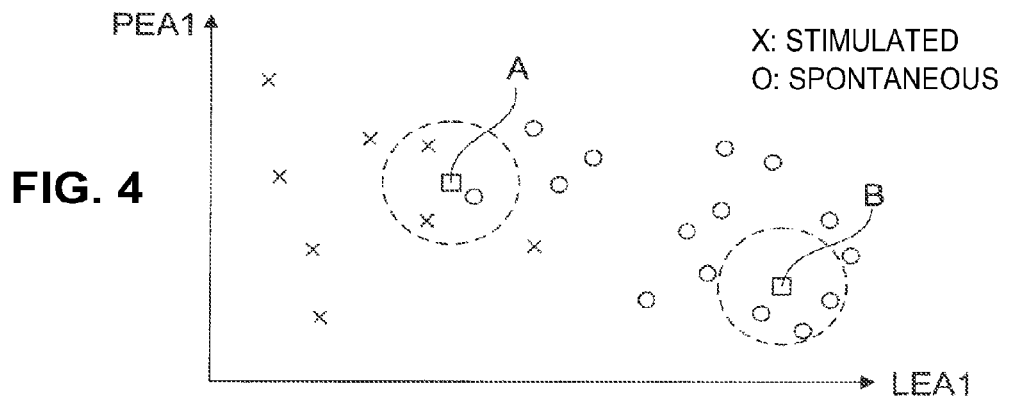
FIGS. 4 and 5 illustrate the position in a two-dimensional space, of the various measurement points identified for situations of stimulated rhythm and spontaneous rhythm, and partitioning the space into two classes defining the capture or the absence of capture.
Figure 5:
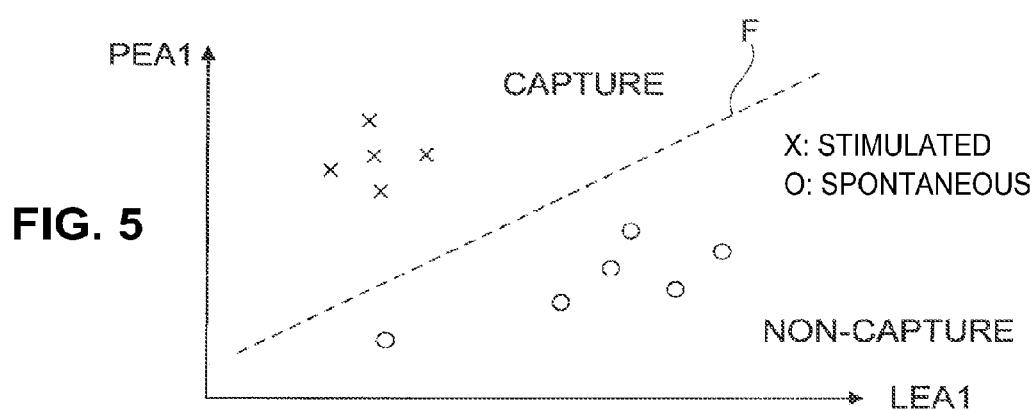
Figure 6:
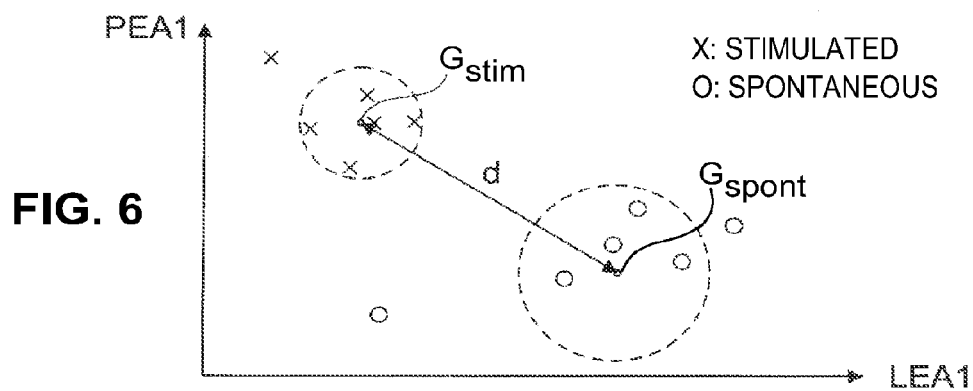
FIG. 6 shows, in a two-dimensional space, the step of checking the distance between the classes previously defined.

Each of the pairs of values {PEA1, LEA1} is a vector representative of the analyzed EA1 component that can be graphically represented by a point in the plane (PEA1, LEA1) as shown in FIGS. 4 and 5.

The example that is described with n=2 and wherein the indicators are PEA1 and LEA1 is in no way limiting, however, and it should be understood that it is possible to perform the analysis on vectors of dimension n>2 including other indicators, alternatively or in addition. Thus, among the representative indicators, temporal indicators can be used, such as:

The moment of occurrence of the EA1 component peak, counted from the origin of the analysis window [0-300 ms]. This moment can notably be calculated such as the average of two timings, the occurrence of the minimum peak $t_m$ and the occurrence of the maximum peak $t_M$ of the EA signal of the EA1 component (see FIGS. 2a and 2b);

The moments of beginning $t_{start}$ and/or of end $t_{end}$, respectively, of the EA1 component (see above for the method these moments are defined);

The moment of the maximum of the power envelope $t_{max, NRG}$, and

The same moments for the PEA2 component.

It is also possible to select indicators representative of the morphology of the EA1 component, such as:

the signal to noise ratio SNR, which can be defined by:

$$\text{SNR\_EA1} = \frac{PEA1}{(2)(\sigma\_\text{noise})}$$

$\sigma$_noise being the standard deviation of the signal considered as "noise", that is to say the signal contented in the EA2 useful signal, with the exception of the segment $\lfloor t_{EA2\_start}, t_{EA2\_end} \rfloor$ corresponding to the EA2 component itself;

the contrast value, given by a formula such as:

$$\text{contrast\_EA1} = \frac{PEA1}{(2)(\sigma_{EA1\_window})}$$

$\sigma_{EA1\_window}$ being the standard deviation of the signal contained in the [0, 300 ms] window;

the entropy, given by a formula such as:

$$\text{entropy\_EA1} = \sum_{EA1\_window} -(\text{average\_ea\_cycles}_i(t) \cdot \log10(\text{average\_ea\_cycles}_i(t)))$$

This amount reflects the "degree of order" of the signal: if the signal is close to white noise, entropy is high, but if it is "ordered," the entropy is lower; and the cumulative energy, calculated from the area under the NRG Energy envelope curve.

Other characteristic indicators may also be used in conjunction, such as:

values of the characteristic amplitudes of the EA4 component, including the peak-to-peak on the window [−200 ms, 0 ms]. It is known that the EA4 component happens between the beginning of the atrial activity (P wave in the case of an ECG, or the detection of the atrial depolarization on the lead in the case of an implantable device) and the beginning of the EA1 component. One skilled in the art is referred to EP 2189180 A1 and its counterpart US Patent Publication No. 2010/0125308 (both assigned to Sorin CRM S.A.S., previously known as ELA Medical), the disclosures of which are hereby incorporated herein by reference, for details on the method to collect and analyze this EA4 component.

Figure 3:
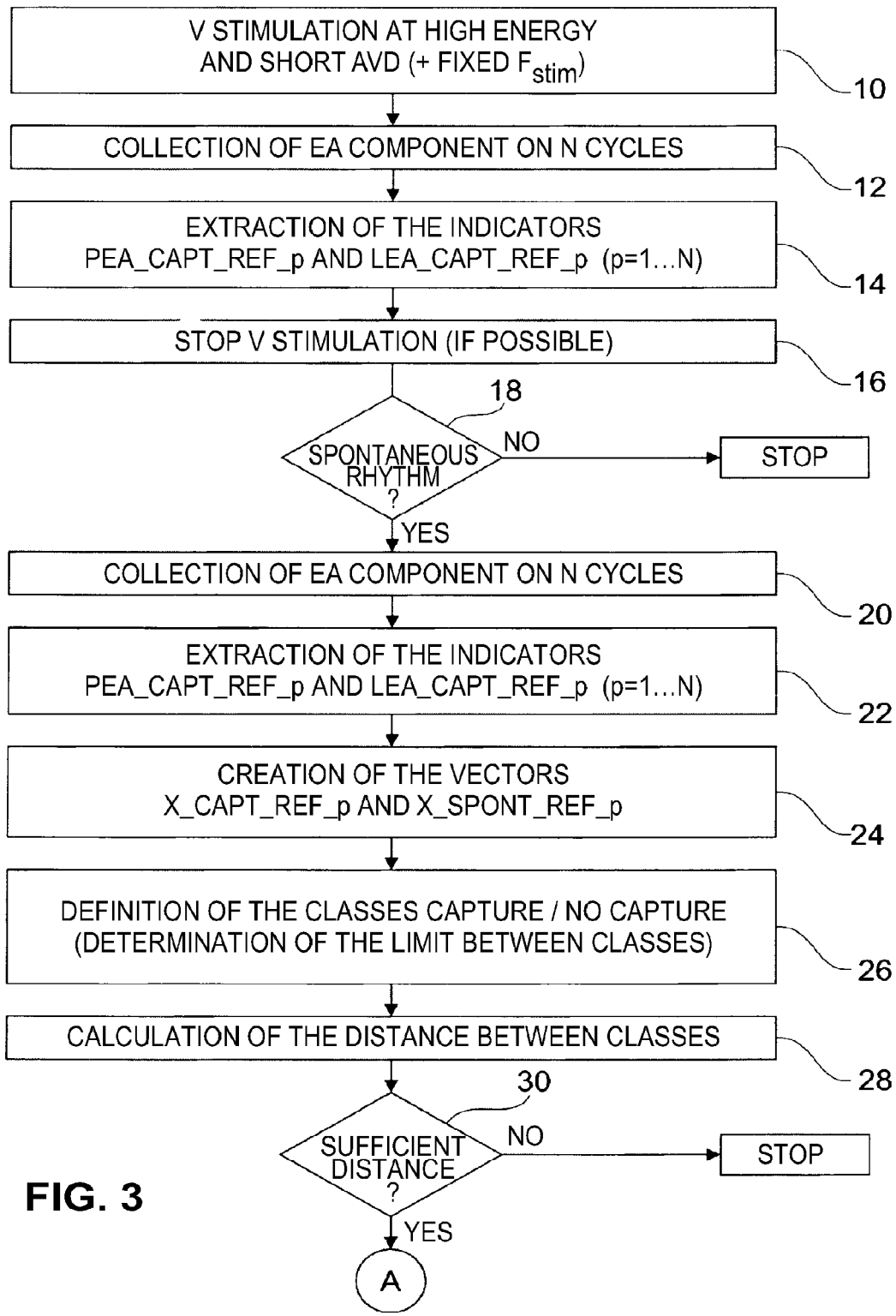
FIG. 3 is a flow chart of a process for obtaining a reference EA component, in the presence of a capture and then in spontaneous rhythm.

FIG. 3 shows the various steps of the initial phase of the method of the present invention, by defining two classes of references (presence or absence of a capture), which are then used for the capture test.

First (block 10) the ventricle is stimulated under conditions enabling the capture, with a relatively high energy stimulating pulse for pacing and a short atrioventricular delay AVD. To avoid variations of rhythm that could disrupt the collection of the EA component, it is also possible to stabilize the heart rate by stimulating the heart through the atrium with a fixed atrial pacing frequency $f_{stim}$.

The EA1 (and/or EA2) component is then collected and averaged over N successive cycles (block 12), typically N=5, as explained above.

The indicators that were chosen are then extracted from the EA component (block 14). In the example above wherein n=2 and these indicators are the amplitude of the PEA peak and the length of the EA1 component LEA1, these indicators extracted from the N=5 successive cycles are: PEA_capt_ref_p and LEA_capt_ref_p (p=1 . . . 5).

Then the ventricular stimulation is stopped (block 16), of course, if it is possible (e.g., in the absence of a complete atrioventricular block).

The presence of a spontaneous rhythm is then sought (test 18) and, if it is present, according to the same method as before, the collection of the EA component over N=5 cycles and the extraction of the corresponding PEA_spont_ref_p and LEA_spont_ref_p, indicators (blocks 20 and 22, similar to blocks 12 and 14) are performed.

The p vectors X_capt_ref_p and the p vectors X_spont_ref_p are then formed from the indicators previously extracted (block 24).

The next step (block 26) is to find a rule for separating of the vectors X_capt_ref_p and X_spont_ref_p into two distinct classes. These classes then allow for a new current vector X from a new stimulation configuration, to determine the presence or absence of a capture according to the classification assigned to this new current vector.

Several methods can be applied to define the rule separating the two classes.

A first technique is to operate separately on the two indicators (that is to say, the two coordinates of the vector), for example, by use of simple threshold detectors, the thresholds for each indicator being selected for a predetermined sensitivity/selectivity compromise (e.g., sensitivity>90% and specificity>95%). Both tests are then combined together by one vote, for example, an AND logical function.

Another technique, preferably used, is to operate directly on two-dimension vectors (or more generally n-dimension vectors, in the case of n>2 indicators extracted from the EA1 component). A given vector can thus be graphically represented by a point in the vector space, including a point in the plane (LEA1, PEA1) in the example given here, as illustrated in FIGS. 4 and 5.

One method' used is the method of the "K-nearest neighbours" (KNN), applied on vectors of indicators, and illustrated in FIG. 4.

The various distances between the vector to test (A or B in FIG. 4) and all vectors of the training base are calculated for this purpose. The K nearest vectors of the vector to be tested (in the example shown, K=3) are then selected and the majority class is assigned to the vector to test, the division occurring between two classes. Thus, in the illustrated example, for the vector A wherein two of the three closest neighbours are part of the "stimulated" class (X), the vector A is considered as belonging to the "stimulated" class while the vector Bt whose three closest neighbours are all part of the "spontaneous" class (0), is considered as belonging to the "spontaneous" class.

A second method used is to implement a neural network, applied to the vector of indicators. After a learning phase to adjust the internal parameters of the neural network, each new test vector processed by the neural network is assigned in output a class of belonging among the two (in the present example) possible classes. A perceptron neural network can be used, which is a simple linear classifier network with n inputs and one output. More details regarding the implementation of a suitable neural network can be found in: Simon Haykin, Neural Networks: A Comprehensive Foundation (2nd Edition), Prentice Hall, 1998 or in: Christopher M. Bishop, Neural Networks for Pattern Recognition, Oxford University Press, 1995.

A third method is to operate a linear classification by estimation of the pseudo-inverse matrix. The class vector taking the values (1, −1) is defined if X belongs to the class Capt_ref and taking the values (−1, 1) if X belongs to the class Spont_ref. Learning is to compute the matrix W which minimizes the RMSE as follows:

$$W = \underset{\pi}{\mathrm{argmin}} \left( \sum_{Learning\_database} \left( W \cdot \vec{X}_i - Class_i \right)^2 \right)$$

The vectors $X_i$ of the learning base (of Class, class) are the vectors X_spont_ref_p and X_capt_ref_p. The matrix W is given by the following expression:

$$W = [Class] \times [X]^T \times ([X] \times [X]^T)^{-1}$$

[X] being the matrix resulting from the concatenation of vectors $X_i$:

$$[X] = [X\_capture\_REF_1, X\_capture\_REF_2, \ldots, X\_spont\_REF_1,]$$

and [Class] being the matrix resulting from the concatenation of the Class, vectors associated with the X, vectors.

Calculating the vector S=W×Y=(S1, S2) is sufficient to determine the class of a vector Y to be tested.

Each component of this output vector is a value (between −1 and 1) that the classifier gives each class. Assigning the class associated with the maximum value to Y is sufficient (if this is S1, Y belongs to the class Capt_ref).

FIG. 5 illustrates the simple case of the space (LEA1, PEA1) divided into two half-spaces with a boundary F which is a line defining the boundary between the two areas capture/non-capture.

But according to the chosen approach, the interzone boundary can also be formed by line segments, a circle, a parabola, or any other geometric shape. This limit may also result in a logical condition, for example, in the case of the KNN, the membership condition of a point X to a zone is determined by looking at the majority ownership area of the K points which are the nearest of X.

It can also be proposed to a user to manually adjust the limit, by drawing it or by moving it on a graph (not necessarily a straight line), or by entering the coordinates of two points belonging to the limit, if this limit is a straight line.

Advantageously, once the two classes are defined, a step of checking the distance between classes is implemented (block 28 in FIG. 3) in order to assess whether the just established classification is really discriminant.

The inter-class distance is defined as the Euclidean distance between the centers of gravity of the two zones (capture/no capture), and it is verified that this distance is sufficiently large compared to the average distances between the elements of each zone in relation to respective centers of gravity. This is particularly illustrated in FIG. 6, wherein d is the distance between the center of gravity $G_{stim}$ of the vectors classified in the "capture" zone, and the center of gravity $G_{spont}$ of the vectors classified in the "no capture" zone. This check can be 'made simply by setting a threshold for deciding that the two zones are sufficiently separated.

Another criterion is to calculate a ratio J, based on the discriminant criterion of Fisher, formed by the relationship between the "distance between the barycenters (m1 and m2) and the "compactness of the classes" $(s_1^2 + s_2^2)$:

$$J = \frac{|m_1 - m_2|^2}{s_1^2 + s_2^2},$$

$$m_1 = \frac{1}{N} \sum_{Class\_1} X_p \text{ and}$$

$$s_i = \sum (X_p - m_i)^2$$

This criterion increases with:

The distance between the barycenters of the projections of class, and with

The "compactness" of the class projections.

If the criterion for sufficient inter-classes distance is not satisfied (block 30), this means there is little or no difference between the EA signal collected by stimulating the ventricle and the EA signal collected in spontaneous rhythm. This may also be the result of a problem with the lead. In such a case, a capture test would be meaningless, and the process is terminated, possibly with an alarm.

Otherwise, that is to say if the indicators identified for the EA signals, respectively in stimulated and in spontaneous configurations, are sufficiently different, the capture test can be performed.

Capture Test and Adjustment of the Stimulation Level

Figure 7:
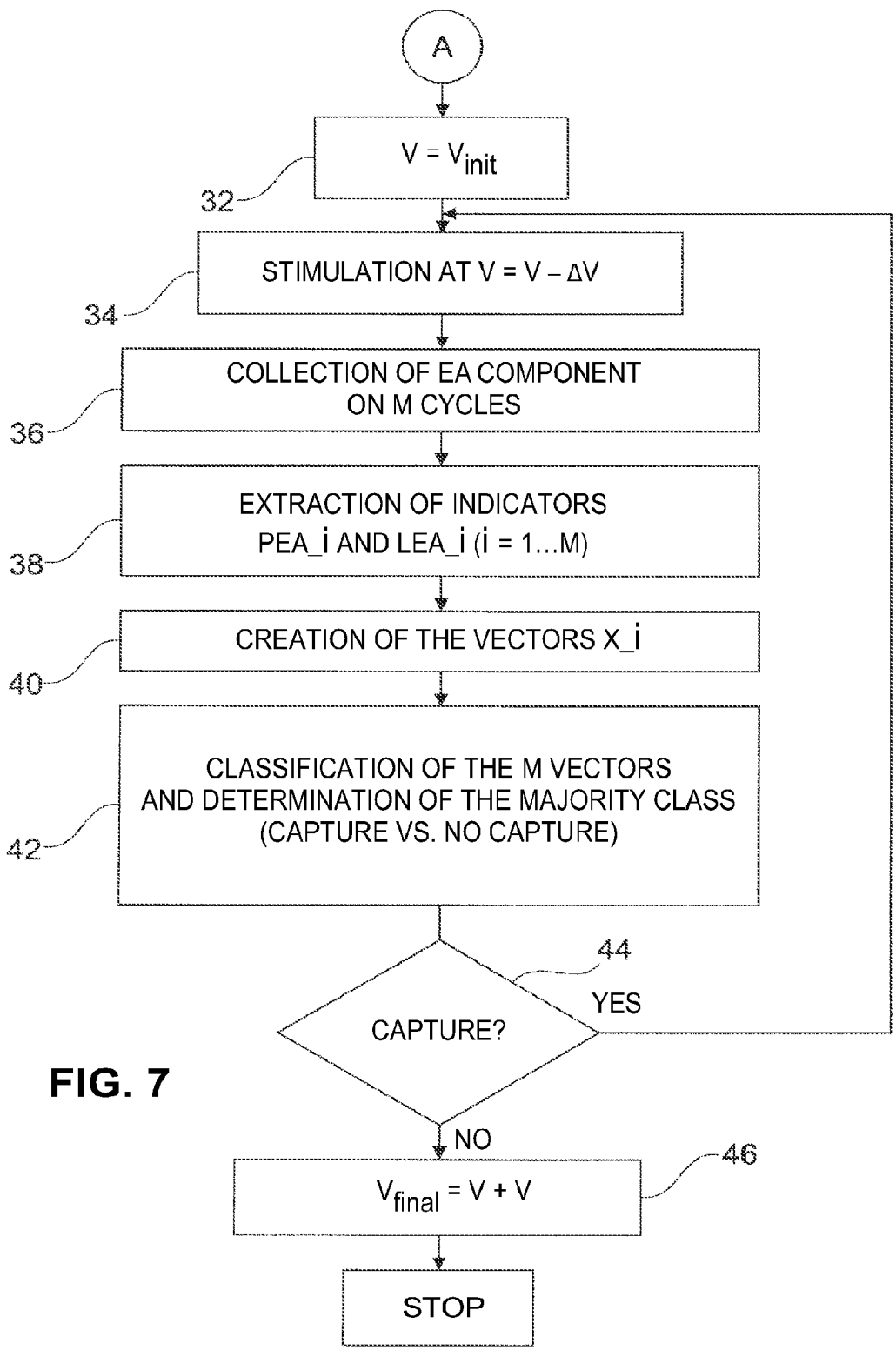
FIG. 7 is a flowchart of a capture test according to the present invention.

The different steps of the ventricular capture test phase are illustrated in FIG. 7. This test of ventricular capture will be described in a search of the threshold (threshold of ventricular pacing). This search is to apply a sequence of stimulation pulses V for ventricular pacing at progressively decreasing energy, and monitoring the EA signal for the presence or absence of a ventricular contraction by the method that will be described. If the contraction is actually present, the device considers that the ventricular pacing delivered an effective stimulation pulse (i.e., there was a ventricular capture). The energy applied to the next ventricular stimulation pulse to be delivered is then reduced, typically by a step of fixed amplitude, for example, $\Delta V$–0.25V.

When loss of capture is detected (i.e., no ventricular contraction is detected in response to a delivered stimulation pulse), the device assumes that the last delivered stimulation is ineffective, and therefore the ventricular pacing threshold is greater than the last applied value. In the latter case, a safety margin of an amount that is greater than the last (ineffective) stimulation pulse can be applied to ensure a ventricular contraction.

The ventricular pacing threshold so determined may be stored in the device memory, may be transmitted to a data collection central station, or used by the implant to change the amplitude of the stimulation pulse applied to the ventricle.

For further details on the algorithms for adjusting the stimulation energy from successive capture tests, one skilled in the art is referred to EP 1080744 A1 and its counterpart U.S. Pat. No. 6,487,451 (both assigned to Sorin CRM S.A.S., previously known as ELA Medical), which disclosures are incorporated herein by reference and describe various techniques for measuring the threshold, of controlling consistency of the measures and of adjusting of the width and amplitude of the stimulation pulse. The algorithms described therein may be implemented using the capture test of the present invention, by analysis of the morphology of the EA signal instead of an electrical detection of the ventricular depolarization.

More precisely, referring to FIG. 7, the stimulation energy level is set at an initial value $V = V_{init}$ (block 32), from which the amplitude of stimulation is iteratively reduced by a step $\Delta V$ (step 34).

The EA (EA1 and/or EA2) component is then collected (block 36) in the manner described above, then the selected indicators corresponding to this component are extracted (block 38), on M cycles, in the example illustrated indicators PEA_i and LEA_i, with i=1 . . . M.

The corresponding vectors X_i are created from the indicators thus extracted (block 40). These M vectors are then classified (block 42) according to one of the methods described above (e.g., KNN, neural network, estimation of the pseudoinverse) and it is chosen that the value of stimulation amplitude V is affected to the majority class among the M.

For M, an odd value is preferably chosen, for example M=3, but it can also be considered in a simplified version only a single pair of indicators PEA__1 and LEA__1 is chosen, thereby reducing the response time of the algorithm.

According to the majority class so defined, it is considered that there is or there is no capture (test 44):

If there was loss of capture, the stimulation pulse is then restored to its previous energy level value (block 46) and the process is considered completed, to the extent it is considered that this level of stimulation is the lowest level to ensure the capture;

If capture is present, then a return to step 34 is done, to further decrease the pacing threshold by a further increment $\Delta V$ and to test again if, for this level of stimulation; the capture is still present, and so on to detect loss of capture.

Note that to avoid the effects of the changes in the rhythm, it is possible to perform the capture test with a fixed stimulation frequency resulting of an atrial controlled stimulation in the same method as that used during the determination of the border between the two classes.

Application to a Biventricular Stimulation Device (CRT Device)

Biventricular pacing of course implies that a capture test is performed on one or the other of the right and left ventricles. In addition, for the optimization of the resynchronization therapy, biventricular stimulation requires to adjust or readjust the interventricular delay WO at regular intervals. This readjustment of the WO is often done by scanning the delay between a minimum WO and a maximum WO, to seek the maximum of a hemodynamic parameter during this scan, the maximum corresponding to the optimum of the WO. The modification can also be achieved by simply changing the value of the WO.

In all cases, the change of WO may affect capture, for example, if stimulation is done with a large WO, a spontaneous depolarization of the stimulated second ventricle may occur before delivery of stimulation to this ventricle. The capture test must thus be repeated for each adjustment of WD.

One skilled in the art will appreciate that the present invention can be practiced by other than the embodiments described herein, which are provided for purposes of illustration and not of limitation.

The invention claimed is:

1. A processor-based method for use with an active implantable medical device for cardiac pacing, resynchronization and/or defibrillation, comprising:
    forming a plurality of first reference endocardial acceleration vectors using a plurality of endocardial acceleration signals acquired using stimulation to cause capture;
    forming a plurality of second reference endocardial acceleration vectors using a plurality of endocardial acceleration signals acquired in a spontaneous rhythm of the patient in the absence of ventricular pacing;
    creating at least a two dimensional space using the first reference endocardial acceleration vectors and the second reference endocardial acceleration vectors, wherein the at least two dimensional space comprises two subspaces corresponding to the presence and absence of capture, respectively; and
    testing for ventricular capture after acquiring a new endocardial acceleration signal, wherein the testing comprises forming a new endocardial acceleration vector for the new endocardial acceleration signal, and wherein the testing comprises determining the presence or absence of capture for the new endocardial acceleration signal based on the position of the new endocardial acceleration vector relative to the two subspaces of the at least two dimensional space.

2. The method of claim 1, further comprising isolating in each endocardial acceleration signal at least one endocardial acceleration component of endocardial acceleration corresponding to a major noise of the heart, and at least one endocardial acceleration component describing the continuous variation of said endocardial acceleration signal in a bounded temporal window corresponding to a fraction of a cardiac cycle.

3. The method of claim 2, further comprising forming the plurality of first reference endocardial acceleration vectors, the plurality of second reference endocardial acceleration vectors, and the new endocardial acceleration vector using at least two indicators extracted from the endocardial acceleration component of each of the plurality of endocardial acceleration signals and the new endocardial acceleration vector.

4. The method of claim 3, wherein the at least two indicators are selected from a group of indicators consisting of: the value of the peak-to-peak amplitude (PEA), the width (LEA), the timing of occurrence of the peak ($t_m$, $t_M$), the start time of the peak ($t_{start}$), and the ending time ($t_{end}$), of endocardial acceleration of the endocardial acceleration component.

5. The method of claim 3, wherein the at least two indicators are selected from a group of indicators consisting of: the signal-to-noise ratio (SNR), the contrast value, the value of entropy, and the cumulative energy, of the endocardial acceleration component.

6. The method of claim 3, wherein creating the at least two-dimensional space having two subspaces comprises applying a threshold criterion separately to each of the indicators of the endocardial acceleration vectors.

7. The method of claim 1, wherein creating the at least two-dimensional space having two subspaces comprises evaluating a distance between the plurality of first reference endocardial acceleration vectors and the plurality of second reference endocardial acceleration vectors for verification of a minimum distance.

8. The method of claim 1, further comprising a method of determining the threshold of ventricular capture, comprising:
    (a) when the presence of capture for the new endocardial acceleration signal has been determined during the testing for ventricular capture step, providing a subsequent stimulation pulse at a lower stimulation energy,
    (b) acquiring a subsequent endocardial acceleration signal resulting from the subsequent stimulation pulse,
    (c) testing for ventricular capture, comprising forming a subsequent endocardial acceleration vector for the subsequent endocardial acceleration signal and determining the presence or absence of capture for the subsequent endocardial acceleration signal based on the position of the subsequent endocardial acceleration vector relative to the two subspaces of the at least two dimensional space,
    (d) repeating steps (a)-(c) until the absence of capture is determined, and
    (e) determining the threshold of ventricular capture based on the energy value of the last stimulation pulse at which capture is present.

9. The method of claim 8, wherein the subsequent stimulation pulse is reduced by a step of fixed amplitude.

10. A system for testing ventricular capture following delivery of a stimulation pulse from an active implantable medical device for cardiac pacing, resynchronization and/or defibrillation, comprising:
    the implantable medical device capable of delivering a stimulation pulse;
    an acceleration sensor for generating an endocardial acceleration signal representative of a patient's endocardiac acceleration;
    a processor configured to:
        form a plurality of first reference endocardial acceleration vectors using a plurality of endocardial acceleration signals acquired by the acceleration sensor when using stimulation sufficient to cause capture;
        form a plurality of second reference endocardial acceleration vectors using a plurality of endocardial acceleration signals acquired by the acceleration sensor in a spontaneous rhythm of the patient in the absence of ventricular pacing;
        create at least a two dimensional space using the first reference endocardial acceleration vectors and the second reference endocardial acceleration vectors, wherein the at least two dimensional space comprises two subspaces corresponding to the presence and absence of capture, respectively; and test for ventricular capture after acquiring a new endocardial acceleration signal, wherein the testing comprises forming a new endocardial acceleration vector for the new endocardial acceleration signal, and wherein the testing comprises determining the presence or absence of capture for the new endocardial acceleration signal based on the position of the new endocardial acceleration vector relative to the two subspaces of the at least two dimensional space.

11. The system of claim 10, wherein the processor is further configured to determine the threshold of ventricular capture, by:
(a) when the presence of capture for the new endocardial acceleration signal has been determined during the testing for ventricular capture step, providing a subsequent stimulation pulse at a lower stimulation energy,
(b) acquiring a subsequent endocardial acceleration signal resulting from the subsequent stimulation pulse,
(c) testing for ventricular capture, comprising forming a subsequent endocardial acceleration vector for the subsequent endocardial acceleration signal and determining the presence or absence of capture for the subsequent endocardial acceleration signal based on the position of the subsequent endocardial acceleration vector relative to the two subspaces of the at least two dimensional space,
(d) repeating steps (a)-(c) until the absence of capture is determined, and
(e) determining the threshold of ventricular capture based on the energy value of the last stimulation pulse at which capture is present.

12. The device of claim 10, wherein the acceleration sensor comprises a sensor selected from among the group consisting of: endocardial sensor, epicardial sensor, external sensor.

13. The system of claim 10, wherein the processor is configured to form the plurality of first reference endocardial acceleration vectors, the plurality of second reference endocardial acceleration vectors, and the new endocardial acceleration vector using at least two indicators extracted from the endocardial acceleration component of each of the plurality of endocardial acceleration signals and the new endocardial acceleration vector.

14. A method of creating a multi-dimensional space comprising two subspaces corresponding to the presence and absence of capture for use in determining the effectiveness of a delivered stimulation pulse, comprising:
delivering stimulation having sufficient energy to cause capture;
acquiring a first plurality of endocardial acceleration signals for a plurality of cardiac cycles following the delivery of stimulation;
extracting at least two indicators from the first plurality of endocardial acceleration signals;
acquiring a second plurality of endocardial acceleration signals for a plurality of cardiac cycles during a spontaneous rhythm of the patient in the absence of stimulation;
extracting at least two indicators from the second plurality of endocardial acceleration signals;
creating a plurality of first reference endocardial acceleration vectors in a multi-dimensional space based on the at least two indicators from the first plurality of endocardial acceleration signals;
creating a plurality of second reference endocardial acceleration vectors in a multi-dimensional space based on the at least two indicators from the second plurality of endocardial acceleration signals; and
defining two subspaces corresponding to the presence and absence of capture based on a rule for separating the plurality of first reference endocardial acceleration vectors from the plurality of second reference endocardial acceleration vectors.

15. The method of claim 14, wherein the at least two indicators are selected from a group of indicators consisting of: the value of the peak-to-peak amplitude (PEA), the width (LEA), the timing of occurrence of the peak ($t_m$, $t_M$), the start time of the peak ($t_{start}$), and the ending time ($t_{end}$), of endocardial acceleration of the endocardial acceleration component.

16. The method of claim 14, wherein the at least two indicators are selected from a group of indicators consisting of: the signal-to-noise ratio (SNR), the contrast value, the value of entropy, and the cumulative energy, of the endocardial acceleration component.

17. The method of claim 14, wherein the rule for separating the plurality of first reference endocardial acceleration vectors from the plurality of second reference endocardial acceleration vectors comprises applying a threshold criterion separately to each of the indicators of the endocardial acceleration vectors.

18. The method of claim 14, wherein the rule for separating the plurality of first reference endocardial acceleration vectors from the plurality of second reference endocardial acceleration vectors comprises graphically representing each vector in the vector space.

19. The method of claim 14, wherein the rule for separating the plurality of first reference endocardial acceleration vectors from the plurality of second reference endocardial acceleration vectors comprises implementing a classification algorithm selected from among the group consisting of: K-nearest neighbors, neural network, and linear classification by estimation of the pseudo-inverse matrix.

20. The method of claim 14, further comprising calculating the distance between the centers of the two subspaces to determine that the distance is sufficiently large compared to the average distances between the elements in each zone.

* * * * *